US012239472B2

(12) United States Patent
Chen et al.

(10) Patent No.: US 12,239,472 B2
(45) Date of Patent: Mar. 4, 2025

(54) SYSTEMS AND METHODS FOR CONTROLLING SCATTER IN COMPUTED TOMOGRAPHY DATA

(71) Applicant: Wisconsin Alumni Research Foundation, Madison, WI (US)

(72) Inventors: Guang-Hong Chen, Madison, WI (US); Ran Zhang, Madison, WI (US); Ke Li, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 228 days.

(21) Appl. No.: 17/971,617

(22) Filed: Oct. 23, 2022

(65) Prior Publication Data

US 2024/0130693 A1 Apr. 25, 2024
US 2024/0225565 A9 Jul. 11, 2024

(51) Int. Cl.
*A61B 6/03* (2006.01)
*A61B 6/00* (2024.01)
*A61B 6/42* (2024.01)

(52) U.S. Cl.
CPC .......... *A61B 6/032* (2013.01); *A61B 6/4441* (2013.01); *A61B 6/482* (2013.01); *A61B 6/5282* (2013.01); *A61B 6/4241* (2013.01)

(58) Field of Classification Search
CPC ..... A61B 6/032; A61B 6/4241; A61B 6/4441; A61B 6/482; A61B 6/5282
See application file for complete search history.

(56) References Cited

U.S. PATENT DOCUMENTS

| | | | | |
|---|---|---|---|---|
| 11,039,801 | B2* | 6/2021 | Drapkin | A61B 6/4233 |
| 11,350,895 | B2* | 6/2022 | Chen | G06T 11/006 |
| 2006/0109949 | A1* | 5/2006 | Tkaczyk | A61B 6/5258 |
| | | | | 378/4 |
| 2007/0205367 | A1* | 9/2007 | Deman | A61B 6/482 |
| | | | | 250/366 |
| 2014/0177785 | A1* | 6/2014 | Funk | A61B 6/035 |
| | | | | 378/9 |

(Continued)

FOREIGN PATENT DOCUMENTS

WO WO-2008012710 A1 * 1/2008 ............. A61B 6/032

OTHER PUBLICATIONS

Ji, X., Zhang, R., Chen, G.-H., and Li, K., "Impact of anti-charge sharing on the zero-frequency detective quantum efficiency of cdte-based photon counting detector system: cascaded systems analysis and experimental validation," Physics in Medicine & Biology 63(9), 095003 (2018).

(Continued)

*Primary Examiner* — Mark R Gaworecki
(74) *Attorney, Agent, or Firm* — Quarles & Brady, LLP

(57) ABSTRACT

A system and method for generating a computed tomography (CT) image of an object includes establishing a narrow-spectrum high-energy bin and other bins with wider-spectrum and lower-energies and acquiring a first dataset using the narrow-spectrum high-energy bin. The method also includes acquiring second or more datasets using the wide-spectrum, low-energy bins, reducing data attributable to scatter from the second or more datasets using the first dataset to create reduced-scatter datasets, and reconstructing CT images of the object from the reduced-scatter datasets.

23 Claims, 7 Drawing Sheets

(56) References Cited

U.S. PATENT DOCUMENTS

2018/0336709 A1* 11/2018 Persson ................ G06T 11/006
2020/0222024 A1* 7/2020 Edic .................... G01N 23/046

OTHER PUBLICATIONS

Love, L. A. and Kruger, R. A., "Scatter estimation for a digital radiographic system using convolution filtering," Medical physics 14(2), 178-185 (1987).

Ning, R., Tang, X., and Conover, D., "X-ray scatter correction algorithm for cone beam ct imaging," Medical physics 31(5), 1195-1202 (2004).

Ohnesorge, B., Flohr, T., and Klingenbeck-Regn, K., "Efficient object scatter correction algorithm for third and fourth generation ct scanners," European radiology 9(3), 563-569 (1999).

Ruhrnschopf and, E.-P. and Klingenbeck, K., "A general framework and review of scatter correction methods in cone beam ct. part 2: scatter estimation approaches," Medical physics 38(9), 5186-5199 (2011).

Zhao, W., Brunner, S., Niu, K., Schafer, S., Royalty, K., and Chen, G.-H., "Patient-specific scatter correction for flat-panel detector-based cone-beam ct imaging," Physics in Medicine & Biology 60(3), 1339 (2015).

Zhu, L., Bennett, N. R., and Fahrig, R., "Scatter correction method for x-ray ct using primary modulation: theory and preliminary results," IEEE transactions on medical imaging 25(12), 1573-1587 (2006).

* cited by examiner

SYSTEMS AND METHODS FOR CONTROLLING SCATTER IN COMPUTED TOMOGRAPHY DATA

CROSS-REFERENCE TO RELATED APPLICATIONS

Not applicable.

STATEMENT REGARDING FEDERALLY SPONSORED RESEARCH

Not applicable.

BACKGROUND

The present disclosure relates to systems and methods for improving computed tomography (CT) systems and, more particularly, to systems and methods for controlling scatter and beam hardening reflected in CT data.

In traditional computed tomography systems, an x-ray source projects a beam that is collimated to lie within an X-Y plane of a Cartesian coordinate system, termed the "imaging plane." The x-ray beam passes through the object being imaged, such as a medical patient, and impinges upon an array of radiation detectors. The intensity of the radiation received by each detector element is dependent upon the attenuation of the x-ray beam by the object, and each detector element produces a separate electrical signal that relates to the attenuation of the beam. The linear attenuation coefficient is the parameter that describes how the intensity of the x-rays changes when passing through an object. Often, the "mass attenuation coefficient" is utilized because it factors out the dependence of x-ray attenuations on the density of the material. The attenuation measurements from all the detectors are acquired to produce the transmission map of the object.

The source and detector array in a conventional CT system are rotated on a gantry within the imaging plane and around the object so that the projection angle at which the x-ray beam intersects the object constantly changes. A group of x-ray attenuation measurements from the detector array at a given angle is referred to as a "view" and a "scan" of the object. These views are collected to form a set of views made at different angular orientations during one or several revolutions of the x-ray source and detector. In a two-dimensional (2D) scan, data is processed to construct an image that corresponds to a 2D slice taken through the object. The prevailing method for reconstructing an image from 2D data is referred to in the art as the filtered back-projection (FBP) technique. This process converts the attenuation measurements from a scan into integers called "CT numbers" or "Hounsfield units", which are used to control the brightness of a corresponding pixel on a display.

Over the past 15 years, much effort has been committed to lowering radiation dose for x-ray CT imaging due to the potential cancer risks associated with the use of ionizing radiation in CT. Many efforts have been made to develop and commercialize systems and methods that enable low-dose CT imaging. Primarily, this has yielded noise-reduction algorithms that seek to reduce the inevitable decreases in SNR as the dose is decreased. However, CT hardware with improved radiation dose efficiency, primarily x-ray detectors such as photon counting detectors, have also been studied and developed to enable low dose CT imaging. Photon counting detector CT (PCD-CT) has been featured as one of the most important advances in low dose CT imaging due to its powerful noise rejection functionality in addition to other advantages such as spectral CT imaging capability. Currently, PCD-CT has been developed by major CT manufacturers for preclinical and, recently clinical evaluations.

PCD-CT is an emerging technology with the potential to improve clinical CT imaging dramatically. By setting energy thresholds, x-ray photons are automatically registered into low-energy and high-energy bins, enabling spectral imaging. In this way, PCD-CT is also able to discriminate based on energy and, thus, is sometimes referred to as energy-discriminating (ED) CT or energy-discriminating and photon-counting (ED-PC) CT. Despite the theoretical improvements in the data available via PCD-CT, numerous factors may substantially impact the accuracy of spectral imaging, including scattered radiation, energy resolution of the detector, and pulse pile-up. For systems with large/wide detectors and cone-beam CT, x-ray scatter may become the major cause of image quality degradation and quantification error due to the increased irradiation area. As a result of scattered radiation, strong cupping artifacts can be observed due to the underestimation of linear attenuation coefficients in the middle area of the object. Existing scatter estimation and correction methods either rely on additional hardware, such as beam-stop arrays and primary modulator, or depend on building physical scatter models after initial reconstruction, such as using Monte Carlo simulation or reprojection techniques. Each of these efforts comes with substantial drawbacks. However, most pointedly, real-time scatter correction is required for many imaging applications in interventional radiology and radiation therapy, and these efforts fall short, either by not sufficiently controlling against scatter or by not being operable in real time. Often, the high computational cost of these methods makes them incompatible with these applications.

Compton scattering is one of the most problematic issues, particularly, in multi-row detector CT for disease diagnoses and cone-beam CT for image guidance in minimally invasive interventions, in radiation therapy, or in heavy ion therapy such as proton therapy. In the Compton scattering process, when an incident photon interacts with the orbital electrons of atoms in the image object, a fraction of the photon energy will be transferred to orbital electrons. This energy transfer process leads to the deflection of x-ray photons from their primary path and these photons deflected from their primary path are referred to as "scatters". Thus, in the course of an x-ray beam interacting with an image object, the scattered photons continuously reduce their energies and change directions, which yields substantial erroneous signals in the detector pixels that are away from the targeted pixels of the primary x-ray beam. These erroneous signals generated by the scattered x-rays are often simply referred to as scatter. In clinical images, the scatter yields artifacts that undermine the clinical value of the images.

Thus, it would be desirable to have systems and methods for CT imaging where the influence of scatter on the acquired data is controlled.

SUMMARY

The present disclosure overcomes the aforementioned drawbacks by providing systems and methods for controlling against scatter undermining the clinical utility of the images. In accordance with some aspects of the disclosure, the systems and methods provided herein can be utilized in a PCD-CT environment. For example, by selecting an energy threshold of the PCD, both primary and scattered photons can be redistributed in the energy bins and then identified to be removed from the underlying data and/or resulting images.

In accordance with one aspect of the disclosure, a computed tomography (CT) medical imaging system is provided that includes an x-ray source configured to deliver x-rays to an object as the x-ray source is rotated about the object and a processor. The processor is configured to control the x-ray source to perform an image acquisition process using a first, high-energy threshold to generate a narrow-spectrum, high-energy, first dataset and at least one second, low-energy threshold to generate at least one wide-spectrum, low-energy second dataset. The processor is also configured to utilize the first dataset to create an image of the object from the second dataset that has reduced scatter artifacts compared to an image reconstructed from the second dataset without using the first dataset. In accordance with another aspect of the disclosure, In accordance with one other aspect of the disclosure, a method is provided for generating a computed tomography (CT) image of an object. The method includes establishing a narrow-spectrum high-energy bin and wide-spectrum, low-energy bin, acquiring a first dataset using the narrow-spectrum high-energy bin, and acquiring at least one second dataset using the wide-spectrum, low-energy bin. The method also includes reducing data attributable to scatter from the wide-spectrum, low-energy second dataset using the first dataset to create a reduced-scatter dataset and reconstructing a CT image of the object from the reduced-scatter dataset.

In accordance with another aspect of the disclosure, a non-transitory, computer readable storage medium is provided having instructions stored thereon that, when executed by a processor, causes the processor to carry out steps. The steps include accessing a narrow-spectrum, high-energy, first dataset, accessing a wide-spectrum, low-energy second dataset, and utilizing the first dataset to create an image of the object from the second dataset that has reduced scatter artifacts compared to an image reconstructed from the second dataset without using the first dataset.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
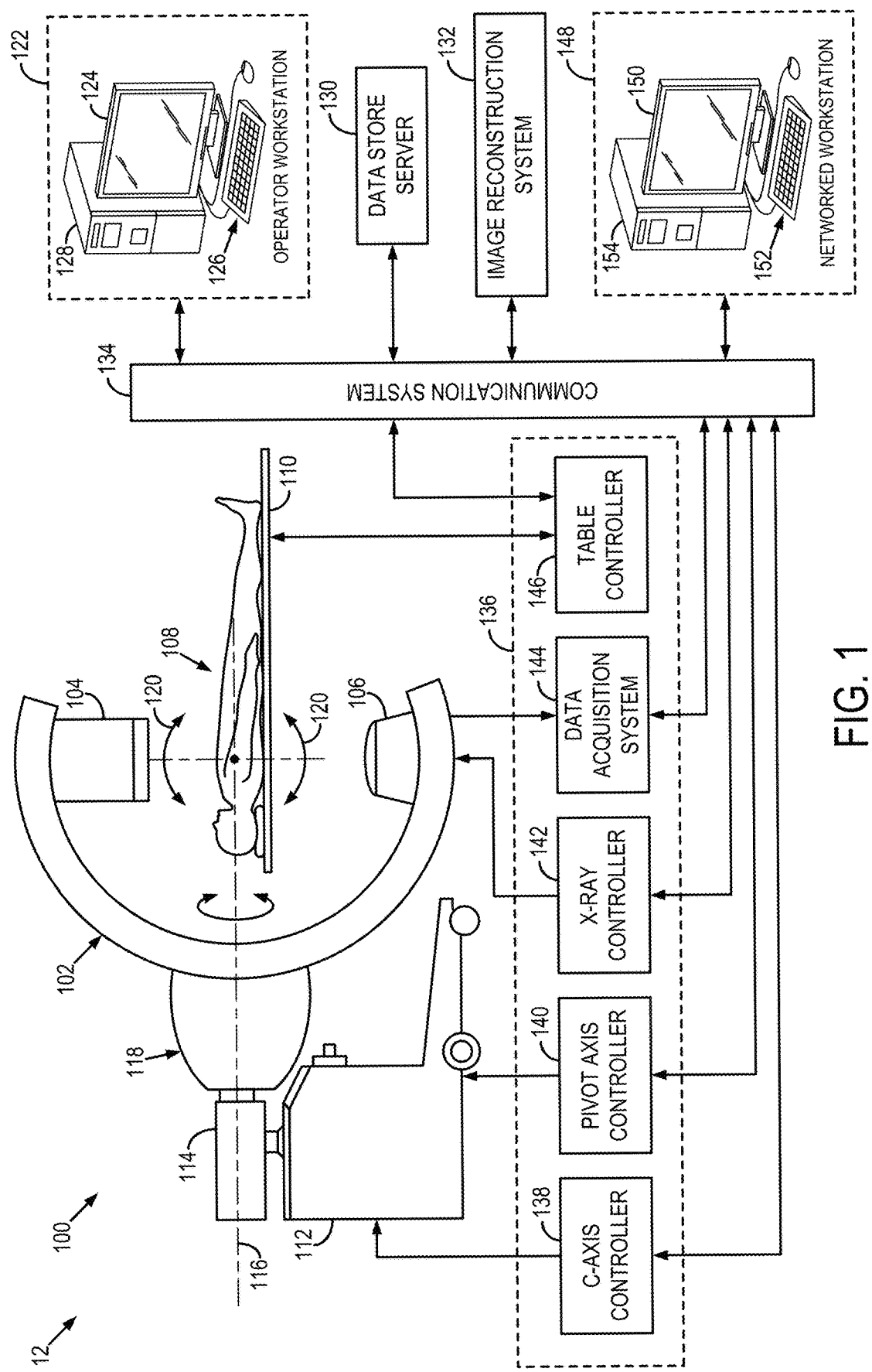
FIG. 1 is a schematic diagram of a C-arm x-ray computed tomography (CT) imaging system configured in accordance with the present disclosure.
Figure 2A:
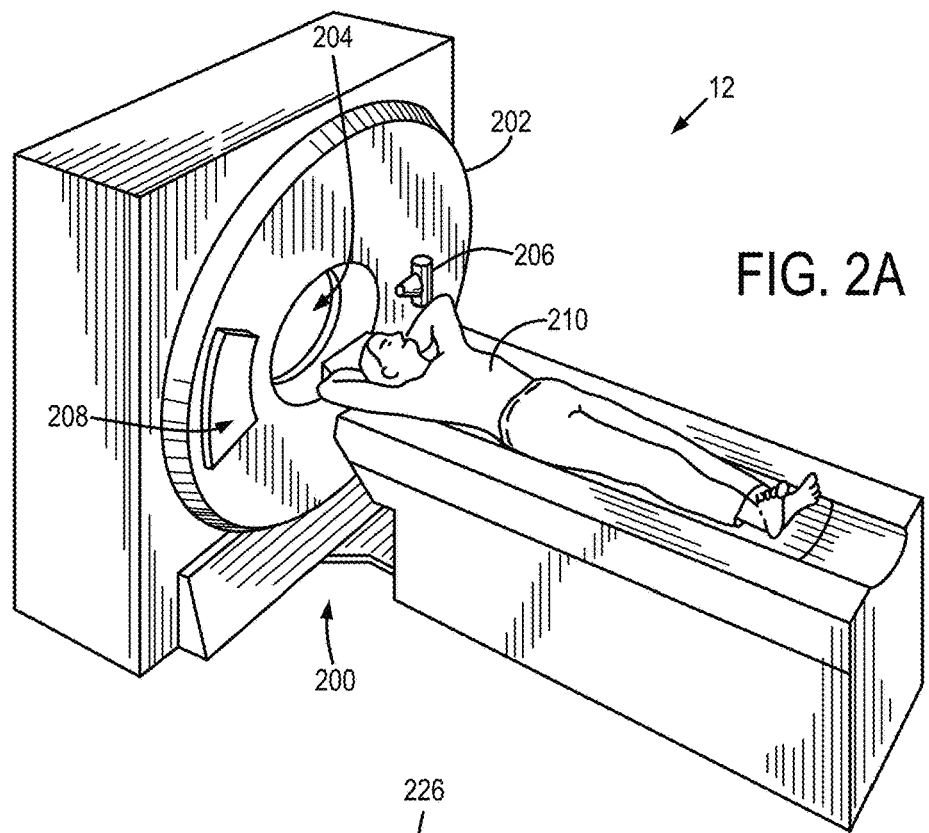
FIG. 2A is a perspective view of an example of an x-ray computed tomography (CT) system.

Referring to FIG. 1, one, non-limiting example of an imaging system 12 that may be configured in accordance with systems and methods provided in the present disclosure is provided. Specifically, in this example, a so-called "C-arm" x-ray imaging system 100 is illustrated for use in accordance with some aspects of the present disclosure. Such an imaging system is generally designed for use in connection with interventional procedures and or radiation therapy procedures. Such systems stand in contrast to, for example, traditional computed tomography (CT) systems 200, such as illustrated in FIG. 2A, which may also serve as an example of the imaging system 12 for use with the systems and methods of the present disclosure.

Referring again to FIG. 1, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which will be described below.

Together, the x-ray detector elements in the one or more x-ray detectors housed in the x-ray detector array assembly 106 sense the projected x-rays that pass through a subject 108. Each x-ray detector element produces a signal that may represent the intensity of an impinging x-ray beam (in the case of a scintillator) or the specific energy or number of x-rays (in the case of an PCD, which may also be referred to as an energy discriminating detector) and, thus, the attenuation of the x-ray beam as it passes through the subject 108. In some configurations, each x-ray detector element is capable of counting the number of x-ray photons that impinge upon the detector and determine the energy (via energy integration) of scattered x-rays.

During a scan to acquire x-ray projection data, the gantry 102 and the components mounted thereon rotate about an isocenter of the C-arm x-ray imaging system 100. The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store server 130, and image reconstruction system 132 may be connected via a communication system 134, which may include any suitable network connection, whether wired, wireless, or a combination of both. As an example, the communication system 134 may include both proprietary or dedicated networks, as well as open networks, such as the Internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system (DAS) 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data are communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122 or on a mobile system or in the cloud. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol (TCP), the Internet protocol (IP), or other known or suitable protocols.

Figure 2B:
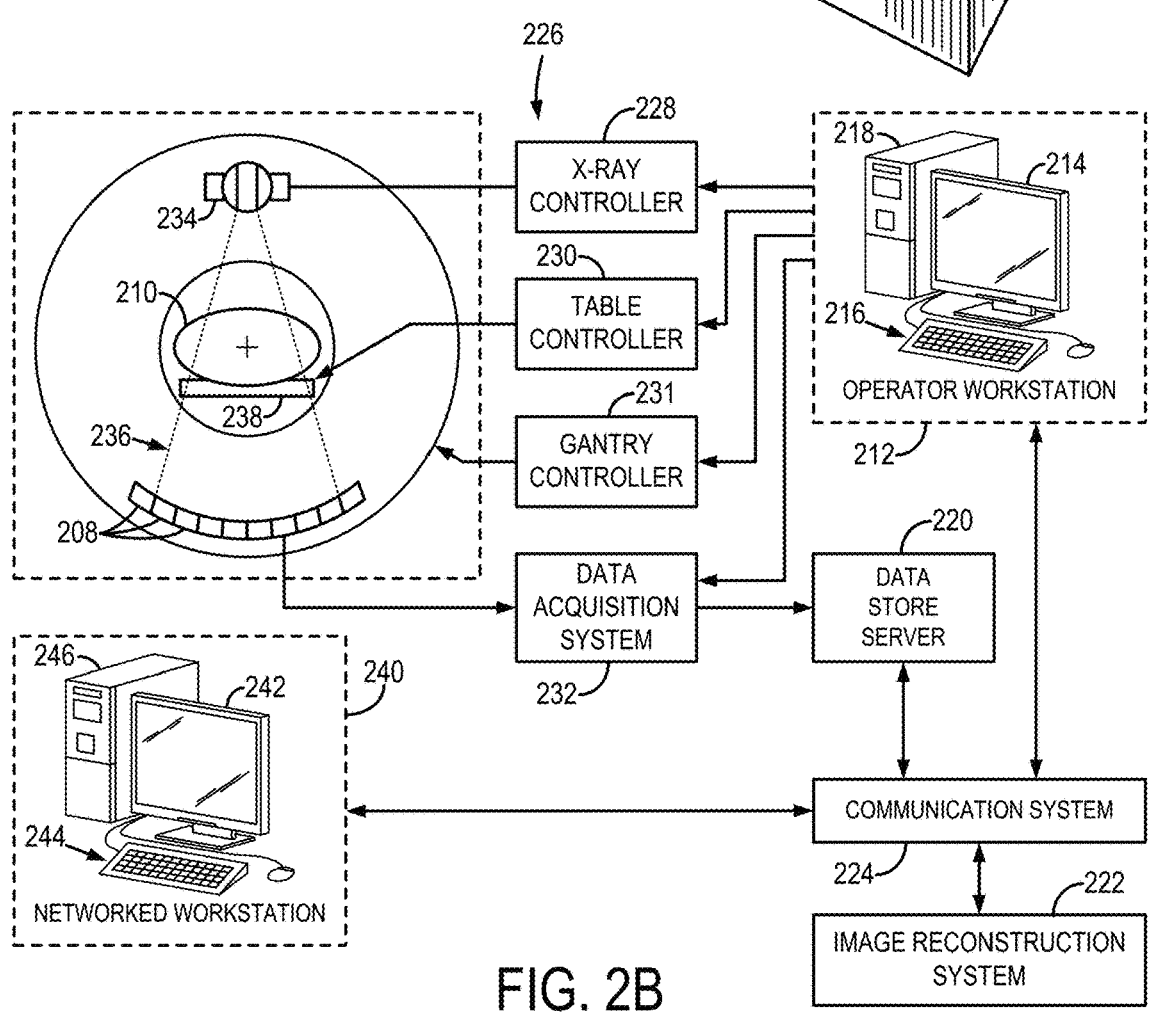
FIG. 2B is a block diagram of CT system, such as illustrated in FIG. 1B.

Similarly, referring to FIGS. 2A and 2B, the imaging system 12 may include a gantry-based CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store sever 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data are communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

The present disclosure recognizes that the scatter-to-primary ratio (SPR) changes with the energy level. With this realization in place, the present disclosure provides systems and methods for using energy discrimination as a tool during data acquisition to identify and remove data corresponding to scatter. In one, non-limiting example, a first energy bin can be established, for example, a quasi-monochromatic high energy bin. Also, a second energy bin that is distinct from the first energy bin can be established. The second energy bin may be a polychromatic low energy bin. In this non-limiting example, a monochromatic high (Mohi) energy bin is used with a polychromatic low (Polo) energy bin. In a PCD-CT system, the energy sensitivity of PCD-CT can be used to establish these bins. This multi-bin (e.g., Mohi-Polo) strategy can yield nearly scatter-free high-energy bin data, which is then used to estimate and correct the scatter in the low-energy bin sinogram data.

Figure 3:
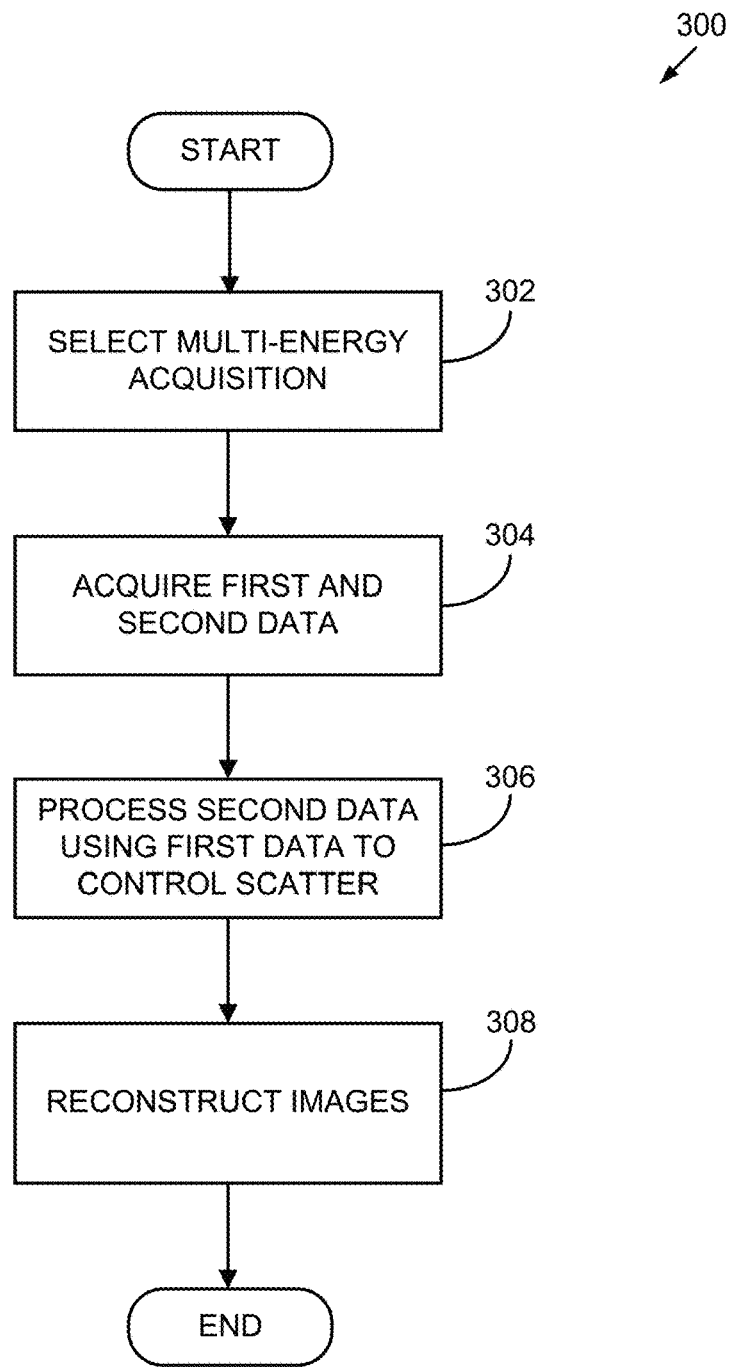
FIG. 3 is a flow chart setting forth non-limiting, example steps of a method in accordance with one aspect of the present disclosure.

Referring to FIG. 3, one non-limiting example a process 300 in accordance with the present disclosure begins with selecting a multi-energy acquisition using a CT system, such as described above with respect to FIGS. 1-2B. The multi-energy acquisition may be coordinated relative to a detection strategy that utilizes multiple bins and associated thresholds. As described above, in a non-limiting example, a first threshold may be used to acquire a first dataset using the narrow-spectrum high-energy bin. Also, a second or more thresholds may be used to acquire additional dataset(s) using the wide-spectrum, low-energy bin(s).

For example, the first and second thresholds may be used to establish a narrow-spectrum, high-energy bin and a wide-spectrum, low-energy bin. In one non-limiting example, the narrow-spectrum, high-energy bin may be referred to monochromatic (or quasi- or substantially-monochromatic) high (Mohi) energy bin and the wide-spectrum, low-energy bin may be referred to as a polychromatic (or quasi- or substantially-polychromatic) low (Polo) energy bin. Additional energy bins may be used. Furthermore, the thresholds used to distinguish between the bins may be selected by a user, pre-selected by a manufacturer of the imaging system or software, or may be automatically selected or calibrated based on the acquisition strategy to be performed, including the energies to be utilized.

In one, non-limiting example, the wide-spectrum, low-energy bin (e.g., Polo) may be established relative to a beam of, for example, 120 kV polychromatic x-rays, or other value. In one, non-limiting example the lowest threshold of the wide-spectrum, low energy bin may be in the rage of 20 keV, or above or below. That is, the lowest energy threshold of the wide-spectrum, low-energy bin(s) may be selected to have an energy level above those that would be affected by electronic noise, but at the lower end of the capabilities of the imaging system, such as 20 to 25 keV, or higher. That is, the specific value of the wide-spectrum, low-energy beam and the bin established by the corresponding threshold can vary, but is separated from the narrow-spectrum, high-energy bin and beam. In this non-limiting example, the first threshold may be set to 20-25 keV to reject electronic noise and second threshold may be set to, for example, 100 keV or 110 keV for a 120 kVp beam, to establish a wide-low-energy spectrum and a narrow-high-energy spectrum.

Thus, the narrow-spectrum high-energy (e.g., Mohi) beam has a high energy, at least as compared to the Polo beam and has a narrow spectrum that is, at least compared to the Polo beam, effectively monochromatic (or quasi- or substantially-monochromatic). That is, as referred to herein monochromatic, does not mean that the Mohi beam must be perfectly monochromatic, but is at least substantially less spectrally diverse than the Polo beam. In addition to be comparatively monochromatic, the narrow-spectrum high-energy beam is at a substantially higher energy level than the Polo beam. In one non-limiting example, the narrow-spectrum high-energy beam can be set in band 10 to 20 keV just below the top energy range that is available to the given CT system based on its tube potential. In one non-limiting the narrow-spectrum high-energy bin may be set at 120 keV. However, again, this can vary and be coordinated with the selected energy of the narrow-spectrum high-energy beam.

Referring to FIG. 3 again, at process block 304, the narrow-spectrum high-energy and Polo data sets are acquired. At process block 306, the wide-spectrum, low-energy data is then processed using the narrow-spectrum high-energy data to control or substantially or entirely remove scatter. In particular, the systems and methods of the present disclosure recognize the energy dependence of Compton scatter and the fact that higher energy bins are less likely to be contaminated by lower energy photons in PCD. Thus, data in the quasi-monochromatic high energy bin will be substantially free of scatter, whereas data in the polychromatic low energy bin will include scatter.

In one non-limiting example, the processing of block 306 may use the energy dependence of linear attenuation coefficients in the low and high energy bins. In this case, $\mu(E_{Low}) = a\mu(E_{High})$ of a given material. Further, the following equation can be used to estimate scatter counts in the wide-spectrum, low-energy bin projections:

$$N_s^{Low} \approx N^{Low} - N_{primary}^{Low} = N^{Low} - N_0^{Low} e^{-p(E_{Low})} = N^{Low} - N_0^{Low} e^{-\alpha p(E_{High})} \quad (1);$$

where is the scatter in the low energy bin, $N^{Low}$ is the measured counts in the low energy bin, $N_{primary}^{Low}$ the primary counts in the low energy bin, $N_0^{Low}$ is the counts of the air scan, $p_f(E_{Low})$ s the measured post-log sinogram of the low energy bin, and $p_f(E_{High})$ is the measured post-log sinogram of the high energy bin. The scaling factor ($\alpha$) may be tuned for different materials, which can be empirically determined or from calibration measurements. To further reduce the noise in the estimated scatter, standard denoising or convolutional scatter kernel fitting can be used at process block 306.

Using the above equation, the narrow-spectrum high-energy bin data can be used to remove scatter from the Polo data at process block 306. Thus, at process block 308, images can be reconstructed from the wide-spectrum, low-energy data that are substantially or completely free of artifacts caused by scatter.

Thus, a computed tomography (CT) medical imaging system is provided that includes an x-ray source configured to deliver x-rays to an object as the x-ray source is rotated about the object and a processor. The processor is configured to control the x-ray source to perform an image acquisition process to produce two sets of data with the following characteristics: 1) the first data set is the one at the high-energy end and the one with a narrow-energy bin to ensure that the recorded signals are produced by photons with nearly the same energies; 2) the second data set is the one to record all other signals except the ones recorded in the first data set. Sometimes, the second data set is further divided into multiple data sets with finer differentiations in the energy ranges.

The processor is also configured to utilize the first dataset to create an image of the object that is almost free of scatter artifacts. This first data set and the associated image can be further used to correct the scatters inevitably recorded in the second data set. As a result of this correction step, the second data set is also nearly free of scatters and can be used to reconstruct a second image that is also nearly free of scatter artifacts.

The processor is also configured to utilize the first dataset to create an image of the object that is almost free of beam-hardening artifacts. The first data set can also be used as a calibration data set to correct beam hardening effect that inevitably exists in the second data set due to the fact that the second data set records low energy signals with broad x-ray energy ranges. After this correction step, the reconstructed image of the object from the second data set also has reduced beam hardening artifacts.

The processor is also configured to utilize the first data set to create an image of the object that is almost free of metal artifacts as a result of the characteristic of this data set that is both nearly mono-chromatic and nearly free of scatters. This first image can be used to identify metal traces in both the reconstructed image and the corresponding data set. The identified metal traces can then be used as a mask to mask out the corresponding metal traces in the second data set with broad energy spectrum. The first data set is also used to normalize the second data set with the metal traces being masked out. A data interpolation scheme is then used to estimate the data for the metal traces in this normalized data set. After the data interpolation, a de-normalization step is then used to convert the data back to generate a new second data set with metal traces being corrected. This metal traces corrected data set is then used to reconstruct the second data set that is nearly free of metal artifacts.

SIMULATIONS AND EXPERIMENTS

Figure 4:
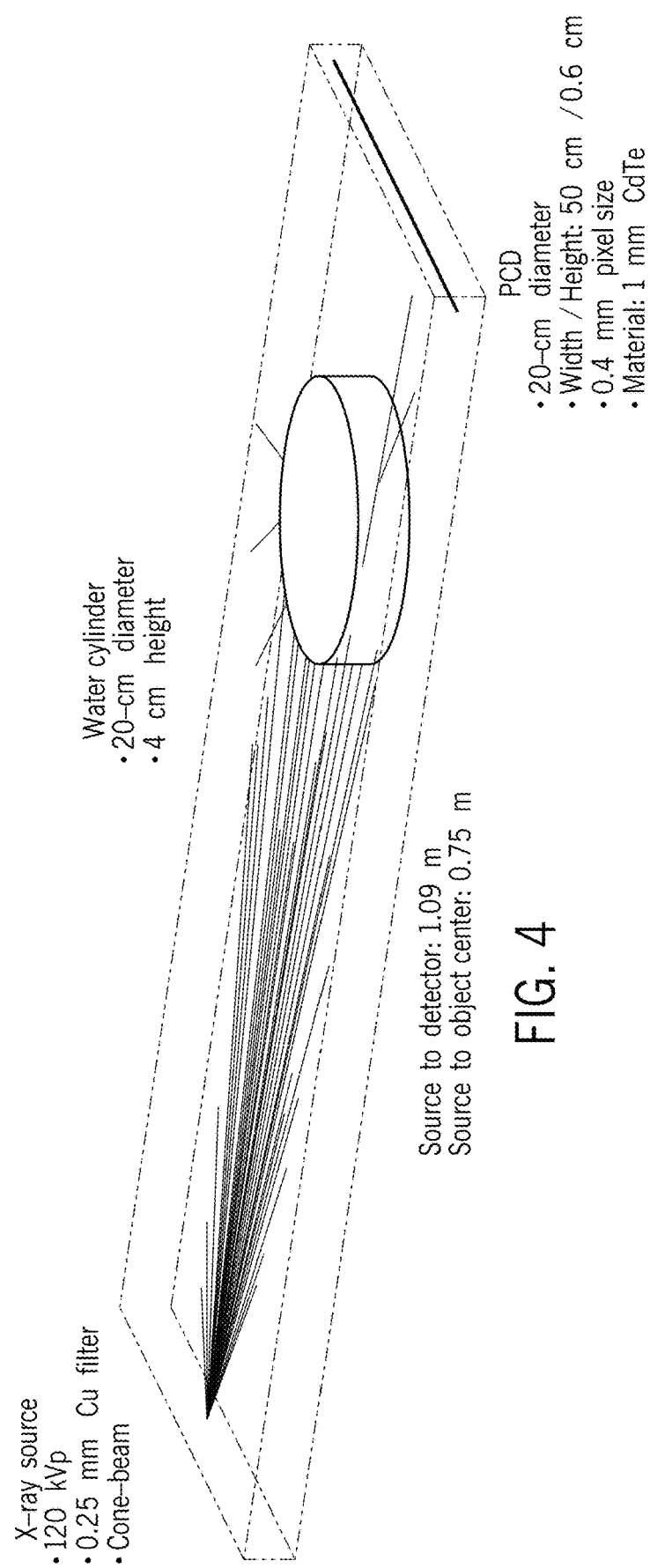
FIG. 4 is a schematic illustration of a Monte Carlo simulation used to validate systems and methods provided in the present disclosure.

A Monte Carlo simulation toolkit, GATE, was used to model photon interactions in the phantom and detector. The geometry and parameters used in the Monte Carlo simulation are shown in FIG. 4. This setup represents a cone-beam CT with 4-cm z-coverage. The energy information of every photon detected by the detector pixels was recorded. For each photon, the number of scattering events (Compton and Rayleigh) in the phantom was also recorded, which is used to identify primary and scattered photons for SPR calculation. To simulate the realistic energy response of the PCD, an experimentally validated model was applied.

Figure 5B:
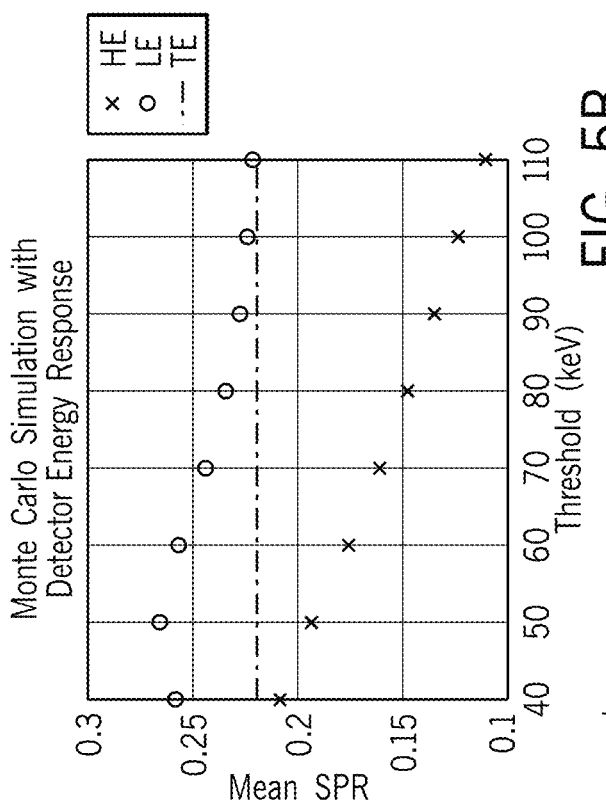
FIG. 5B is a graph showing results of a Monte Carlo simulation with a realistic detector energy response.
Figure 5A:
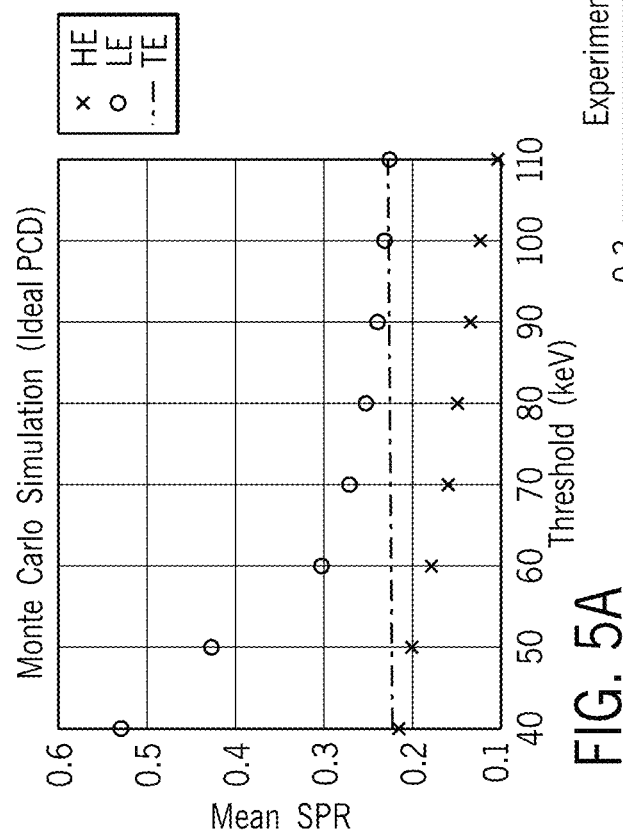
FIG. 5A is a graph showing results of a Monte Carlo simulation using a photon counting detector with an ideal energy response.

FIG. 5A-5B shows Monte Carlo simulation results of mean SPR of a 20 cm water phantom when using an ideal PCD (FIG. 5A) and with a realistic energy response (FIG. 5B). The Monte Carlo result with a realistic energy response model matches well with the experimental measurements (FIG. 5C).

Figure 5C:
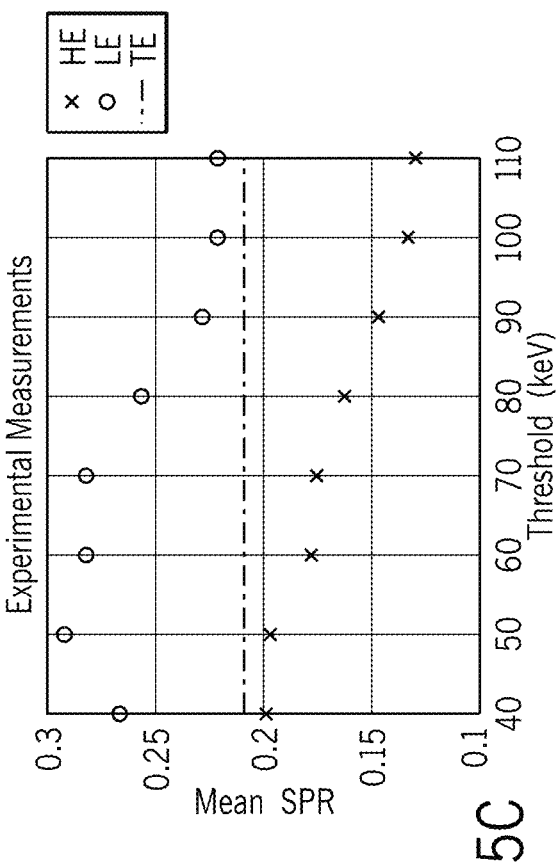
FIG. 5C is a graph showing results of experimental results.
Figure 6:
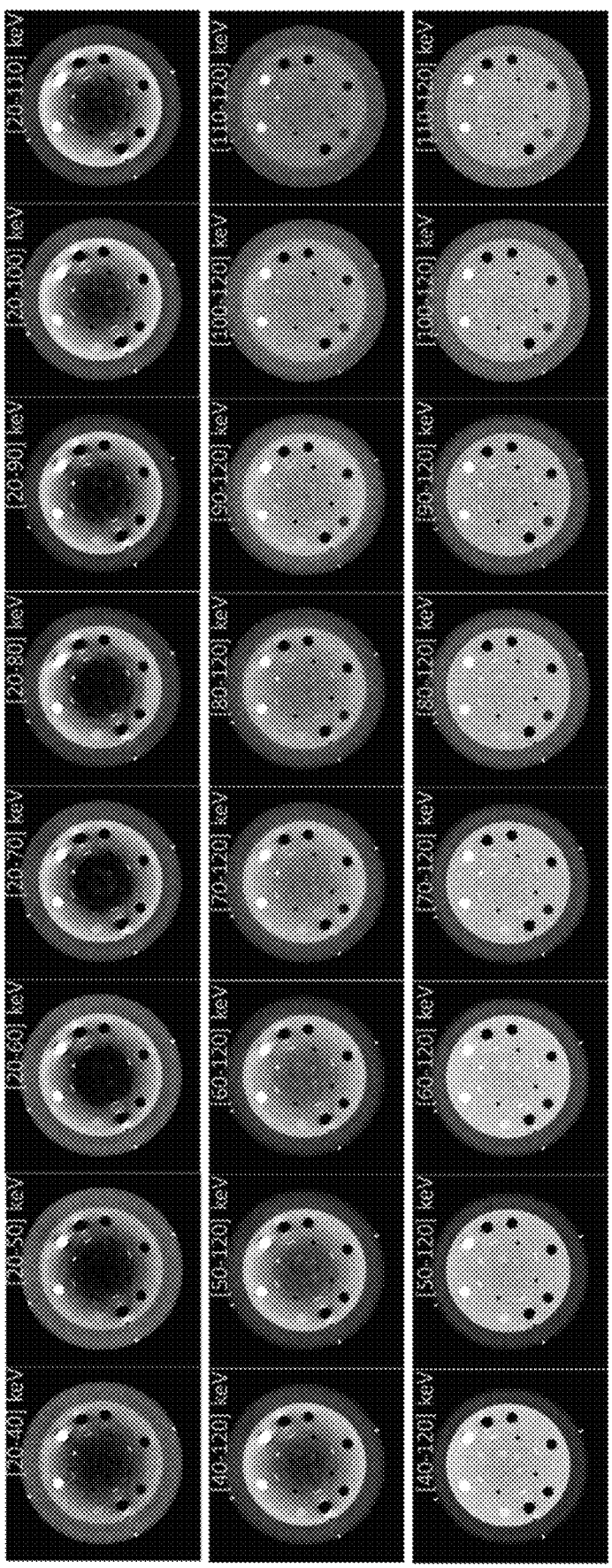
FIG. 6 is a set of correlated images showing experimental cone-beam PCD-CT images of a phantom acquired using a variety of energy bin settings and their corresponding scatter-free reference images acquired using a narrow collimation.

Referring to FIG. 5C, SPR measurements show that the high energy bin always has a lower SPR than the low energy bin and SPR of the high energy bin decreases linearly with increasing energy threshold. As a result of significantly reduced SPR, the present disclosure recognizes that, for a very high energy threshold, the high energy bin is nearly free of scatter artifact. This can be further seen in the images of FIG. 6, for example, from the [110-120] keV bin. As can be seen in FIG. 6, the cupping artifact is only caused by scatter, not beam-hardening.

Figure 7:
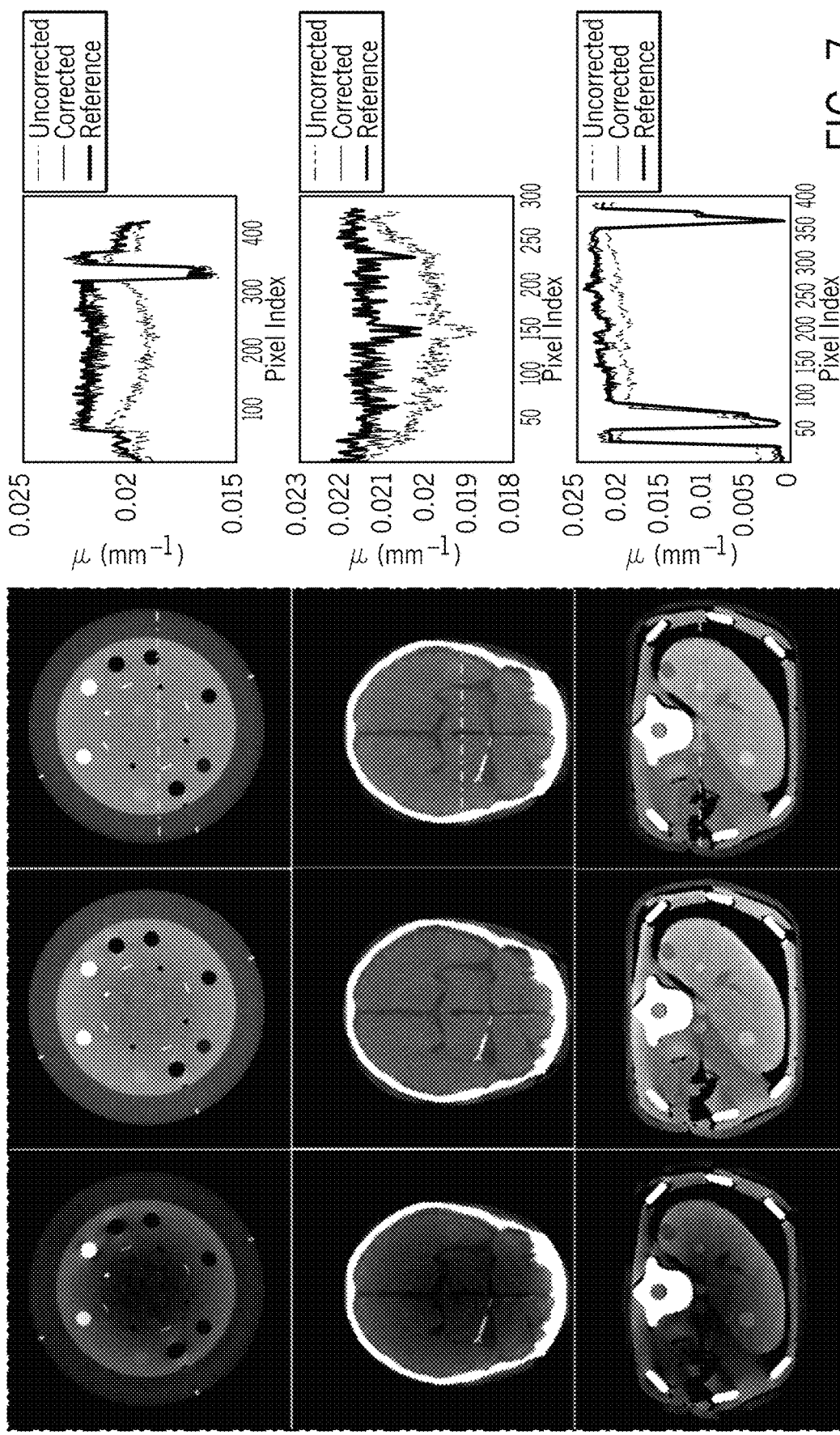
FIG. 7 is a set of correlated images and graphs showing scatter correction results in accordance with the present disclosure.

Utilizing a scatter-free narrow-spectrum, high-energy data, scatter in the Polo energy bin, can be effectively corrected as described above. In one non-limiting example, a narrow-spectrum, high-energy bin of 110-120 keV and a wide-spectrum, low-energy bin of 20-110 keV was used. FIG. 7 shows the scatter correction results for three different phantoms using these bins. The correction was applied directly in the sinogram domain without initial reconstruction. In the top row of FIG. 7, low energy bins with 4 cm collimation are provided. In the middle row of FIG. 7, high energy bins with 4 cm collimation are provided. In the bottom row of FIG. 7, high energy bins with 0.7 cm collimation were used.

Finally, FIG. 8 shows a set of images and graphs are provided to show the effect of scatter correction. In FIG. 8, an $\alpha=1.03$ was used for the Catphan phantom (top row) and an $\alpha=1.10$ was used for the head (middle row) and abdominal phantom (bottom row).

Thus, the above-described demonstrates that scatter-to-primary ratio changes with the energy threshold in photon counting CT and provides systems and methods to utilize this realization to create CT images with reduced scatter. Both Monte Carlo simulations and experimental measurements demonstrated a significantly reduced SPR in the high-energy bin projection data and reduced scatter artifacts in the reconstructed CT images. A system and methods for data acquisition and image reconstruction, referred to herein as Mohi-Polo, is provided. During image acquisition, a high energy threshold is utilized that generates a quasi-monochromatic high energy bin and a second lower threshold is used to create a polychromatic low energy bin. Utilizing the free or nearly scatter-free high-energy bin data, the scatter artifacts in the low-energy bin are estimated and corrected.

As used herein, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The present invention has been described in terms of one or more preferred embodiments, and it should be appreciated that many equivalents, alternatives, variations, and modifications, aside from those expressly stated, are possible and within the scope of the invention.

The invention claimed is:

1. A computed tomography (CT) medical imaging system comprising:
    an x-ray source configured to deliver x-rays to an object as the x-ray source is rotated about the object;
    a processor configured to:
        control the x-ray source to deliver x-rays to the object;
        perform an image acquisition process using a first, high-energy detection threshold to generate a narrow-spectrum, high-energy, first dataset and at least one second, low-energy detection threshold to generate at least one wide-spectrum, low-energy second dataset; and
        create an image of the object from the second dataset that has been processed using the first dataset to reduce scatter artifacts compared to an image reconstructed from the second dataset without using the first dataset.

2. The system of claim 1, wherein the first, high-energy detection threshold and the second low-energy detection threshold are selected such that the energy ranges of the narrow-spectrum, high-energy, first dataset and the wide-spectrum, low-energy second dataset do not overlap.

3. The system of claim 1, wherein the first, high-energy detection threshold is selected to use an energy proximate to a maximum x-ray energy produced by the x-ray source.

4. The system of claim 1, wherein the first, high-energy detection threshold and the second low-energy detection threshold are selected to create a low-energy bin between 25 keV and 110 keV and the x-ray source delivers a beam at 120 kV.

5. The system of claim 1, further comprising using the first dataset as a calibration dataset to correct beam hardening effects or metal artifacts in the second dataset.

6. The system of claim 1, wherein utilizing the first dataset includes using an energy dependence of linear attenuation coefficients in the narrow-spectrum, high-energy, first dataset to remove data attributable to scatter from the wide-spectrum, low-energy second dataset.

7. The system of claim 6, further comprising estimating scatter counts in the wide-spectrum, low-energy second dataset using:

$$N_s^{Low} \gg N^{Low} - N_{primary}^{Low} = N^{Low} - N_0^{Low} e^{-p_l(E_{Low})} = N^{Low} - N_0^{Low} e^{-\alpha p_l(E_{High})}$$

where $N_s^{Low}$ is a variable representing scatter in the wide-spectrum, low-energy second dataset; $N^{Low}$ is a variable representing measured counts in the wide-spectrum, low-energy second dataset; $N_{primary}^{Low}$ is a variable representing primary counts in the wide-spectrum, low-energy second dataset; $N_0^{Low}$ is a variable representing counts of in an air scan performed with the CT system; $p_l(E_{Low})$ is a variable representing measured post-log sinogram of the wide-spectrum, low-energy second dataset; $P_1(E_{High})$ is a variable representing measured post-log sinogram of the narrow-spectrum, high-energy dataset; and a is a scaling factor that is selected for materials expected in the object.

8. The system of claim 1, wherein the CT system includes a c-arm gantry.

9. The system of claim 1, wherein the first dataset and the second dataset are acquired simultaneously or the first dataset and the second dataset are photon-counting datasets.

10. A method of generating a computed tomography (CT) image of an object, the method comprising:
    establishing a narrow-spectrum high-energy detection bin and wide-spectrum, low-energy detection bin;
    acquiring a first dataset using the narrow-spectrum high-energy detection bin;
    acquiring at least one second dataset using the wide-spectrum, low-energy detection bin;
    reducing data attributable to scatter from the wide-spectrum, low-energy second dataset using the first dataset to create a reduced-scatter dataset; and
    reconstructing a CT image of the object from the reduced-scatter dataset.

11. The method of claim 10, wherein the first, high-energy detection bin and the second, low-energy detection bin do not overlap.

12. The method of claim 10, wherein the first dataset was acquired using a tube potential proximate to a maximum tube potential of an x-ray source.

13. The method of claim 12, wherein the wide-spectrum, low-energy is selected to be between 25 keV and 110 keV and the narrow-spectrum high-energy detection bin is above 110 keV.

14. The method of claim 10, further comprising using the first dataset as a calibration dataset to correct beam hardening effects or metal artifacts in the second dataset.

15. The method of claim 10, wherein reducing data attributable to scatter includes using an energy dependence of linear attenuation coefficients in the first dataset to remove data attributable to scatter from the second dataset.

16. The method of claim 10, further comprising estimating scatter counts in the second dataset using:

$$N_s^{Low} \gg N^{Low} - N_{primary}^{Low} = N^{Low} - N_0^{Low} e^{-p_l(E_{Low})} = N^{Low} - N_0^{Low} e^{-\alpha p_l(E_{High})}$$

where $N_s^{Low}$ is a variable representing scatter in the second dataset; $N^{Low}$ is a variable representing measured counts in the dataset; $N_{primary}^{Low}$ is a variable representing primary counts in the second dataset; $N_0^{Low}$ is a variable representing counts of in an air scan; $p_l(E_{Low})$ is a variable representing measured post-log sinogram of the second dataset; $p_l(E_{High})$ is a variable representing measured post-log sinogram of the first dataset; and α is a scaling factor that is selected for materials expected in the object.

17. A non-transitory, computer readable storage medium having instructions stored thereon that, when executed by a processor, causes the processor to carry out steps comprising:
    accessing a narrow-spectrum, high-energy, first dataset, wherein the first dataset is computed tomography (CT) data;
    accessing a wide-spectrum, low-energy second dataset, wherein the second dataset is CT data; and
    creating an image of an object from the second dataset that has been processed using the first dataset to reduce scatter artifacts compared to an image reconstructed from the second dataset without using the first dataset.

18. The storage medium of claim 17, further comprising using the first dataset as a calibration dataset to correct beam hardening effects or metal artifacts in the second dataset.

19. The storage medium of claim 17, wherein utilizing the first dataset includes using an energy dependence of linear attenuation coefficients in the narrow-spectrum, high-energy, first dataset to remove data attributable to scatter from the wide-spectrum, low-energy second dataset.

20. The storage medium of claim 17, further comprising estimating scatter counts in the wide-spectrum, low-energy second dataset using:

$$N_s^{Low} \rangle N^{Low} - N_{primary}^{Low} = N^{Low} - N_0^{Low} e^{-pl(E_{Low})} = N^{Low} - N_0^{Low} e^{-\alpha pl(E_{High})}$$

where $N_s^{Low}$ is a variable representing scatter in the wide-spectrum, low-energy dataset; $N^{Low}$ is a variable representing measured counts in the wide-spectrum, low-energy second dataset; $N_{primary}^{Low}$ is a variable representing primary counts in the wide-spectrum, low-energy second dataset; $N_0^{Low}$ is a variable representing counts of in an air scan performed with a CT system; $p_l(E_{Low})$ is a variable representing measured post-log sinogram of the wide-spectrum, low-energy second dataset; $p_l(E_{High})$ is a variable representing measured post-log sinogram of the narrow-spectrum, high-energy dataset; and a is a scaling factor that is selected for materials expected in the object.

21. The storage medium of claim 17, wherein narrow-spectrum, high-energy, first dataset and the wide-spectrum, low-energy second dataset were acquired with non-overlapping spectra or tube potentials.

22. A computed tomography (CT) medical imaging system comprising:
an x-ray source configured to deliver x-rays to an object as the x-ray source is rotated about the object;
a processor configured to:
control the x-ray source to deliver x-rays to the object;
perform an image acquisition process using a first, high-energy detection threshold to generate a narrow-spectrum, high-energy, first dataset and at least one second, low-energy detection threshold to generate at least one wide-spectrum, low-energy second dataset; and
utilize the first dataset to create an image of the object from the second dataset that has reduced scatter artifacts compared to an image reconstructed from the second dataset without using the first dataset, wherein utilizing the first dataset includes using an energy dependence of linear attenuation coefficients in the narrow-spectrum, high-energy, first dataset to remove data attributable to scatter from the wide-spectrum, low-energy second dataset.

23. A non-transitory, computer readable storage medium having instructions stored thereon that, when executed by a processor, causes the processor to carry out steps comprising:
accessing a narrow-spectrum, high-energy, first dataset, wherein the first dataset is computed tomography (CT) data;
accessing a wide-spectrum, low-energy second dataset, wherein the second dataset is CT data; and
utilizing the first dataset to create an image of an object from the second dataset that has reduced scatter artifacts compared to an image reconstructed from the second dataset without using the first dataset, wherein utilizing the first dataset includes using an energy dependence of linear attenuation coefficients in the narrow-spectrum, high-energy, first dataset to remove data attributable to scatter from the wide-spectrum, low-energy second dataset.

* * * * *

UNITED STATES PATENT AND TRADEMARK OFFICE
CERTIFICATE OF CORRECTION

PATENT NO. : 12,239,472 B2
APPLICATION NO. : 17/971617
DATED : March 4, 2025
INVENTOR(S) : Guang-Hong Chen et al.

Page 1 of 1

It is certified that error appears in the above-identified patent and that said Letters Patent is hereby corrected as shown below:

In the Specification

Column 9, Eq. (1), Line 10, "$N_{primary}^{Low}$" should be --$N_{primary}^{Low}$--.

Column 9, Line 13, "$N_{primary}^{Low}$" should be --$N_{primary}^{Low}$--.

In the Claims

Claim 7, Column 11, Line 58, "$N_{primary}^{Low}$" should be --$N_{primary}^{Low}$--.

Claim 7, Column 11, Line 64, "$N_{primary}^{Low}$" should be --$N_{primary}^{Low}$--.

Claim 16, Column 12, Line 44, "$N_{primary}^{Low}$" should be --$N_{primary}^{Low}$--.

Claim 16, Column 12, Line 48, "$N_{primary}^{Low}$" should be --$N_{primary}^{Low}$--.

Claim 20, Column 13, Line 14, "$N_{primary}^{Low}$" should be --$N_{primary}^{Low}$--.

Claim 20, Column 13, Line 19, "$N_{primary}^{Low}$" should be --$N_{primary}^{Low}$--.

Signed and Sealed this
Third Day of June, 2025

Coke Morgan Stewart
*Acting Director of the United States Patent and Trademark Office*